(12) United States Patent
Rabinovitch et al.

(10) Patent No.: US 9,383,374 B2
(45) Date of Patent: *Jul. 5, 2016

(54) METHODS TO DETERMINE SUSCEPTIBILITY TO TREATMENT WITH LEUKOTRIENE MODIFIERS

(71) Applicant: NATIONAL JEWISH HEALTH, Denver, CO (US)

(72) Inventors: Nathan Rabinovitch, Denver, CO (US); Erwin Gelfand, Englewood, CO (US)

(73) Assignee: National Jewish Health, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/177,441

(22) Filed: Feb. 11, 2014

(65) Prior Publication Data

US 2014/0364452 A1 Dec. 11, 2014

Related U.S. Application Data

(63) Continuation of application No. 12/404,984, filed on Mar. 16, 2009, now Pat. No. 8,685,740.

(60) Provisional application No. 61/036,771, filed on Mar. 14, 2008.

(51) Int. Cl.
*A61K 31/47* (2006.01)
*G01N 33/50* (2006.01)
*G01N 33/88* (2006.01)
*G01N 33/497* (2006.01)

(52) U.S. Cl.
CPC ............... *G01N 33/88* (2013.01); *A61K 31/47* (2013.01); *G01N 33/497* (2013.01); *G01N 2033/4975* (2013.01); *G01N 2800/24* (2013.01); *G01N 2800/52* (2013.01); *Y10T 436/177692* (2015.01)

(58) Field of Classification Search
None
See application file for complete search history.

(56) References Cited

U.S. PATENT DOCUMENTS 8,685,740 B2   4/2014  Rabinovitch et al.

OTHER PUBLICATIONS

Whelan et al (Pediatric Pulmonology, 2003, vol. 36, pp. 413-420).*
Currie et al. "Leukotriene C4 synthase polymorphisms and responsiveness to leukotriene antagonists in asthma." British Journal of Clinical Pharmacology, Oct. 2003, vol. 56, No. 4, pp. 422-426.
Dahlen et al., "Improvement of Aspirin-Intolerant Asthma by Montelukast, a Leukotriene Antagonist", Am J Respir Crit Care Med, vol. 165, pp. 9-14, 2002.
Kharitonov et al., "Exhaled Biomarkers", Chest 2006;130;1541-1546.
Krawiec et al., "Leukotriene Receptor Antagonists", Semin Respir Crit Care Med 23(4):399-410, 2002.
"Leukotriene Modifiers", Family Allergy & Asthma, available at www.familyallergy.com/therapy/print/leukotriene_modifiers.asp.
Leung et al. "Clinical and Technical Factors Affecting pH and Other Biomarkers in Exhaled Breath Condensate," Pediatric Pulmonology, 2006, vol. 41, pp. 87-94.
Nuijsink et al. "Urinary eosinophil protein X in children with atopic asthma." Mediators of Inflammation, accepted Mar. 12, 2007, vol. 2007, Article ID 49240, pp. 1-6.
Product References, Aerocrine, available at www.aerocrine.com/en-us/NIOX-MINO/References, accessed Mar. 12, 2009, 3 pages.
Rabinovitch et al., "Exposure to tobacco smoke increases leukotriene E4-related albuterol usage and response to montelukast", J Allergy Clin Immunol, vol. 121, No. 6, Jun. 2008, pp. 1365-1371.
Rabinovitch et al., "Smoky, and they banned it! Lessons learned from smoking bans and their effects on public health", J Allergy Clin Immunol, 2008, vol. 122, No. 3, 542-543.
Rabinovitch et al., "Urine leukotriene E4 levels are associated with decreased pulmonary function in children with persistent airway obstruction", J Allergy Clin Immunol 2006; 118:635-40.
Rabinovitch et al., "Urine LTE4 Levels and Lung Function Declines are Highly Correlated in Urban Children with Moderate to Severe Asthma Despite Use of Inhaled Corticosteriods and Long-acting Bronchodilators", J Allergy Clin Immunol, Feb. 2006 (abstract only).
Rabinovitch, "Urinary Leukotriene E4", Immunol Allergy Clin N Am 27 (2007) 651-664.
Reinero et al. "An Experimental Model of Allergic Asthma in Cats Sensitized to House Dust Mite or Bermuda Grass Allergen," International Archives of Allergy and Immunology, Oct. 2004, vol. 135, No. 2, pp. 117-131.
Stempel et al., "Defining the responder in asthma therapy", J Allergy Clin Immunol 2005;115:466-9.
Szefler et al., "Characterization of within-subject responses to fluticasone and montelukast in childhood asthma", J Allergy Clin Immunol 2005;115:233-42.
Zeiger et al. "Response profiles to fluticasone and montelukast in mild-to-moderate persistent childhood asthma," Journal of Allergy and Clinical Immunology, Jan. 2006, vol. 117, No. 1, pp. 45-52.
International Preliminary Report on Patentability for Application No. PCT/US2009/037306, mailed Sep. 23, 2010.
Extended Search Report for European Patent Application No. 09720738.5, dated Mar. 9, 2011 5 pages.

* cited by examiner

*Primary Examiner* — Karen Canella
(74) *Attorney, Agent, or Firm* — Sheridan Ross P.C.

(57) ABSTRACT

The present invention provides a method of determining the susceptibility of a subject to treatment with a leukotriene modifier by determining the subject's cysteinyl leukotriene (CysLT) level and the subject's level of eosinophilic airway inflammation and identifying a subject with a high ratio of CysLT levels to eosinophilic airway inflammation as susceptible to treatment with the leukotriene modifier. Also discussed is a method of treatment of subjects who are susceptible to treatment that includes administering a leukotriene modifier to such a subject.

15 Claims, 2 Drawing Sheets

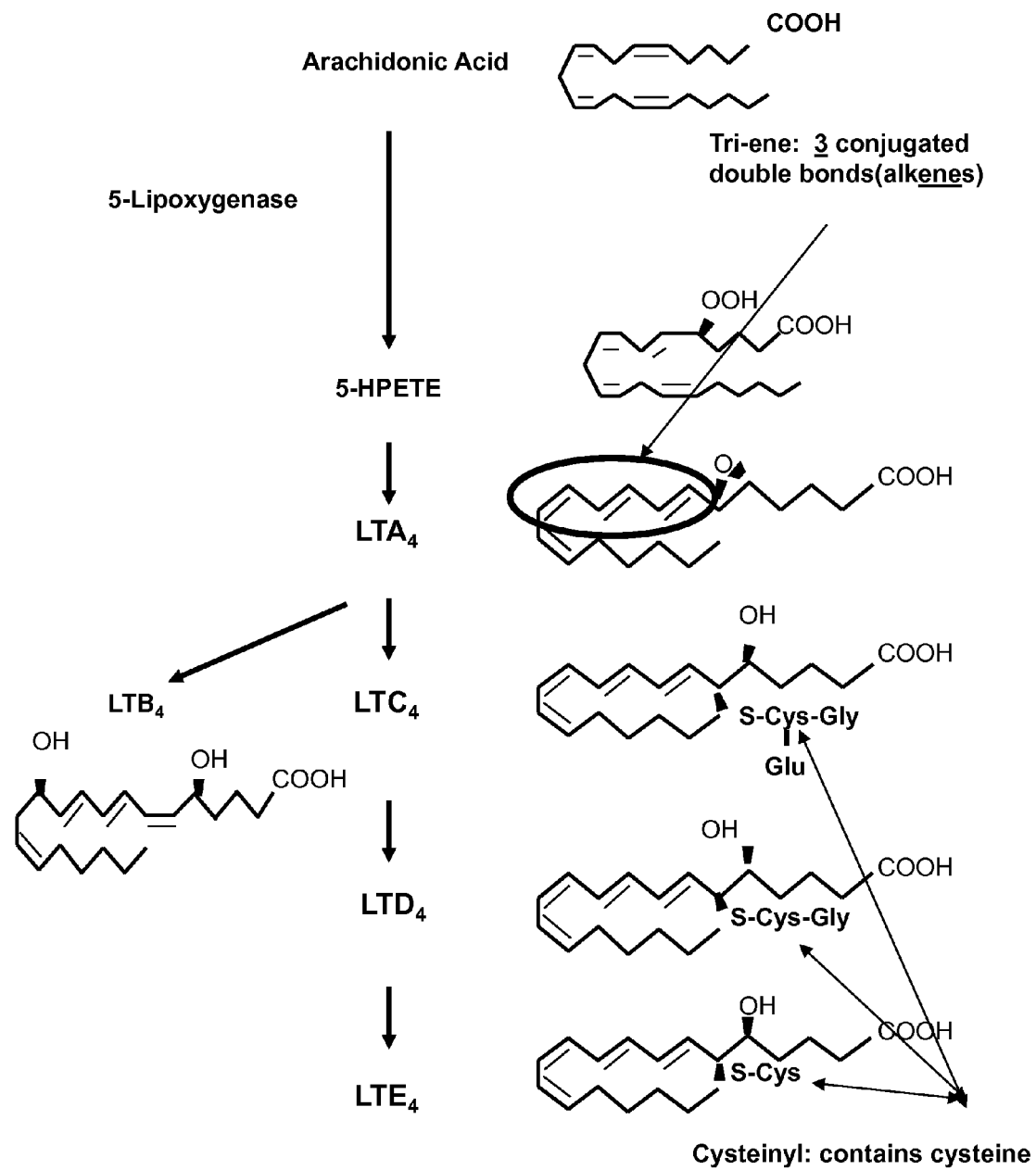
Fig 1: Major Steps in CysLT Formation

Fig. 2A
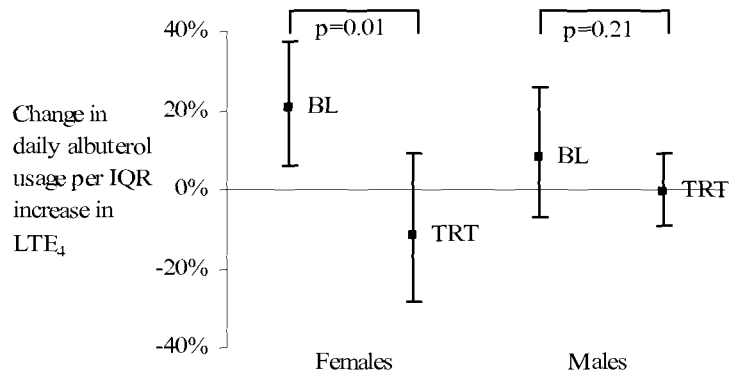
Fig. 2B
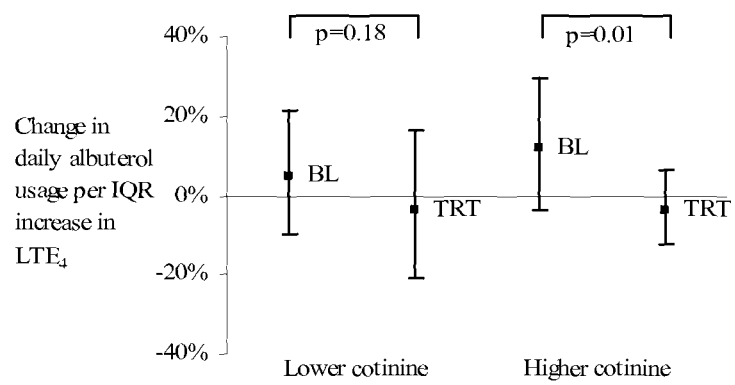
Fig. 2C
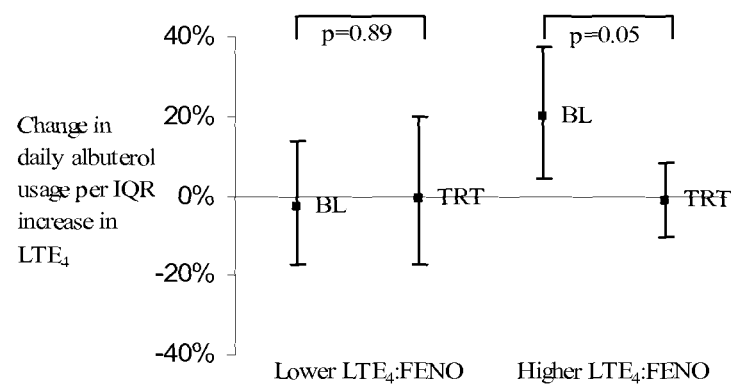
Fig 2

METHODS TO DETERMINE SUSCEPTIBILITY TO TREATMENT WITH LEUKOTRIENE MODIFIERS

CROSS REFERENCE TO RELATED APPLICATIONS

The present application is a continuation of U.S. application Ser. No. 12/404,984, filed Mar. 16, 2009, and issued Apr. 1, 2014, which claims the benefit of priority under 35 U.S.C. §119(e) from Provisional Patent Application Ser. No. 61/036,771, filed on Mar. 14, 2008. Provisional Patent Application Ser. No. 61/036,771 and U.S. application Ser. No. 12/404,984 are incorporated herein by reference in its entirety.

GOVERNMENT SUPPORT

This invention was supported in part with funding provided by NIH/NIEHS K23 Grant No. ES015510-01 awarded by the National Institutes of Health. The government has certain rights to this invention.

FIELD OF THE INVENTION

The present invention is directed to a novel method for determining an individual subject's susceptibility to treatment with a leukotriene modifier. Leukotriene modifiers are presently given to many subjects who are not responsive to these medications, in part due to the lack of a reliable method to distinguish subjects susceptible to the treatment from those subjects who are non-responsive.

BACKGROUND OF THE INVENTION

Leukotrienes are a family of lipid mediators derived from arachidonic acid (ARA) through the 5-lipoxygenase pathway. They are produced by various leukocytes, hence the first part of their name (leuko-). The tri-ene part of the name refers to the number (three) of conjugated double bonds (alkenes). Examples of leukotrienes are $LTA_4$, $LTE_4$, $LTC_4$, $LTD_4$, $LTE_4$, and $LTE_4$, with $LTC_4$, $LTD_4$ and $LTE_4$ often called cysteinyl leukotrienes (CysLTs) due to the presence of the amino acid in their structure. The first leukotriene to be synthesized, leukotriene $A_4$ ($LTA_4$), is formed through conversion of ARA located in membrane phospholipids to 5-hydroperoxyeicosatetraenoic (5-HPETE) and $LTA_4$ through membrane-bound 5-lipoxygenase and 5-lipoxygenase-activing protein (FLAP). In human mast cells, basophils, eosinophils, and macrophages, $LTA_4$ converts quickly to either $LTE_4$ (through LTA hydrolase) or $LTC_4$ by $LTC_4$ synthase with the incorporation of glutathione (γ-glutamyl-cysteinyl-glycine). $LTC_4$ is subsequently converted to $LTD_4$ and then to the stable end product $LTE_4$ (FIG. 1) (Rabinovitch, N. Urinary Leukotriene E4. *Immunol. Allergy Clin. N. Am.* 27:651-664, 2007 and Busse W, Kraft M. Cysteinyl leukotrienes in allergic inflammation: strategic target for therapy. *Chest* 2005; 127: 1312-26).

The CysLTs are important mediators of inflammatory reactions and exert powerful effects on vasoconstriction and bronchoconstriction (Doucet M Y, Jones T R, Ford-Hutchinson A W. Responses of equine trachealis and lung parenchyma to methacholine, histamine, serotonin, prostanoids, and leukotrienes in vitro. *Can J Physiol Pharmacol* 1990; 68:379-83; Gyllfors P, Kumlin M, Dahlén S E, Gaber F, Ehrs P O, Dahlen B. Relation between bronchial responsiveness to inhaled leukotriene D4 and markers of leukotriene biosynthesis. *Thorax* 2005 November; 60(11):902-8). CysLTs are thus mediators of inflammatory airway diseases such as asthma and chronic obstructive pulmonary disease (Busse W, Kraft M. Cysteinyl leukotrienes in allergic inflammation: strategic target for therapy. *Chest* 2005; 127:1312-26; Kanwar S, Johnston B, Kubes P. Leukotriene C4/D4 induces P-selectin and sialyl Lewis (x)-dependent alterations in leukocyte kinetics in vivo. *Circ Res* 1995; 77:879-887). In particular, CysLTs have been implicated in asthma worsening triggered by exposure to tobacco smoke.

Clinical studies have demonstrated that leukotriene receptor antagonists (LTRAs) are able to reduce rescue treatment requirements, improve pulmonary function and reduce symptoms in adults and children with asthma (Barnes N, Thomas M, Price D, Tate H. The National Montelukast Survey. *J Allergy Clin Immunology* 2005; 115; 47-54; Becker A, Swern A, Tozzi C A, Yu Q, Reiss T, Knorr B. Montelukast in asthmatic patients 6 years-14 years old with an FEV1>75%. *Curr Med Res Opin* 2004 October; 20 (10): 1651-9). This relationship between CysLTs and asthma severity appears to not be homogenous across populations. For example, a number of studies have reported that female schoolchildren respond more favorably to the LTRA montelukast than boys (Szefler S J, Phillips B R, Martinez F D, Chinchilli V M, Lemanske R F, Strunk R C, et al. Characterization of within-subject responses to fluticasone and montelukast in childhood asthma. *J Allergy Clin Immunol* 2005; 115:233-42; Johnston N W, Mandhane P J, Dai J, Duncan J M, Greene J M, Lambert K, et al. Attenuation of the September epidemic of asthma exacerbations in children: a randomized, controlled trial of montelukast added to usual therapy. *Pediatrics* 2007 September; 120(3): 702-12) and that smoking adults show a greater response than non-smokers (Lazarus S C, Chinchilli V M, Rollings N J, Boushey H A, Cherniack R, Craig T J, et al. Smoking affects response to inhaled corticosteroids or leukotriene receptor antagonists in asthma. *Am J Respir Crit Care Med* 2007 Apr. 15; 175 (8): 783-90). Other studies have reported both that urinary $LTE_4$ excretion increases acutely after tobacco smoking (Fauler J, and Frolich J C. Cigarette smoking stimulates cysteinyl leukotriene production in man. *Eur J Clin Invest* 1997; 27:43-47.) and that levels of FENO are lower in schoolchildren with chronic environmental tobacco exposure (Warke T J, Mairs V, Fitch P S, Ennis M, Shields M D. Possible association between passive smoking and lower exhaled nitric oxide in asthmatic children. *Arch Environ Health* 2003 October; 58(10): 613-6; and Nordvall S L, Janson C, Kalm-Stephens P, Foucard T, Torén K, Alving K. Exhaled nitric oxide in a population-based study of asthma and allergy in schoolchildren. *Allergy* 2005 April; 60(4): 469-75.). Why antileukotriene medications are effective in some subjects and ineffective in others remains unclear. Some studies suggest that susceptibility to LTRAs is related to differences in CysLT levels between individuals (Szefler S J, Phillips B R, Martinez F D, Chinchilli V M, Lemanske R F, Strunk R C, et al. Characterization of within-subject responses to fluticasone and montelukast in childhood asthma. *J Allergy Clin Immunol* 2005; 115:233-42; Cai C, Yang J, Hu S, Zhou M, Guo W. Relationship between urinary cysteinyl leukotriene E4 levels and clinical response to antileukotriene treatment in patients with asthma. *Lung* 2007 March-April; 185 (2): 105-12) while other studies have not observed this relationship (Dahlén S E, Malmstrom K, Nizankowska E, Dahlén B, Kuna P, Kowalski M, et al. Improvement of aspirin-intolerant asthma by montelukast, a leukotriene antagonist. A randomized, double-blind, placebo-controlled trial. *Am J Respir Crit Care Med* 2002; 165: 9-14). As such, it is unclear whether susceptibility is primarily a function of increased CysLT production, differences in pharmacokinetic metabolism of the medication, increased receptor sensitivity or perhaps a more complex interaction with other mediator pathways. Identifying biological and phenotypic characteristics related to CysLT effects and efficacy of LTRAs such as montelukast would allow for more defined clinical evaluations focused on subpopulations most likely to benefit from such treatments.

In previous studies, the relationship between the stable end-product of CysLT metabolism, leukotriene $E_4$ ($LTE_4$) and asthma control was examined (Rabinovitch N, Zhang L, Gelfand E W. Urine leukotriene $E_4$ levels were determined to be associated with decreased pulmonary function in children with persistent airway obstruction. *J Allergy Clin Immunol* 2006 September; 118 (3): 635-40).

While inhaled corticosteroids (ICS) are generally considered more potent than LTRAs and are therefore recommended as first-line therapy (Ducharme F M, Di Salvio F. Anti-Leukotriene agents compared to inhaled corticosteroids in the management of recurrent and/or chronic asthma in adults and children. *The Cochrane Database of Systematic Reviews* 2004, issue 1, Art. No. CD002314) treatment with ICS alone may not adequately control disease in 30% to 40% of patients (Heaney L G, Robinson D S. Severe asthma treatment: need for characterising patients. *Lancet*. 2005 Mar. 12-18; 3 65(9463): 974-6). This could reflect the inability of ICS therapy to reduce leukotriene production in certain subject subsets where this pathway predominates (Manso G, Baker A J, Taylor I K, Fuller R W. In vivo and in vitro effects of glucocorticosteroids on arachidonic acid metabolism and monocyte function in nonasthmatic humans. *Eur Respir J* 1992; 5:712-6; O'Shaughnessy K M, Wellings R, Gillies B, Fuller R W. Differential effects of fluticasone propionate on allergen-evoked bronchoconstriction and increased urinary leukotriene E4 excretion. *Am Rev Respir Dis* 1993; 147:1472-6). Although previous reports suggest that LABAs (long-acting beta-agonist) are superior to LTRAs in combination therapy (Ram F S F, Cates C J, Ducharme F M. Long acting beta-2 agonists versus anti-leukotrienes as add-on therapy to inhaled corticosteroids for chronic asthma. *The Cochrane Database of Systematic Reviews* 2005, Issue 1. Art. No. CD003137), other studies have reported that the addition of montelukast to ICS therapy is similar to LABAs in reducing symptoms and exacerbations of asthma (Ilowite J, Webb R, Friedman B, Kirwin E, Bird S R, Hustad C M, et al. Addition of montelukast or salmeterol to fluticasone for protection against asthma attacks: a randomized, double-blind, multicenter study. *Ann Allergy Asthma Immunol* 2004 June; 9 2(6): 641-8; Bjermer, L, Bisgaard H, Bousquet, J, Fabbri L M, Greening A P, Haahtela, T, et al. Montelukast and fluticasone compared with salmeterol and fluticasone in protecting against asthma exacerbation in adults: one year, double blind, randomized, comparative trial. *BMJ* 2003; 327:891).

SUMMARY OF THE INVENTION

The present invention provides for a method to determine the susceptibility of a subject to treatment with a leukotriene modifier. This method comprises determining the subject's level of cysteinyl leukotriene (CysLT) production. This method further comprises determining the subject's level of eosinophilic airway inflammation; and determining the ratio between the subject's CysLT production and the subject's level of eosinophilic airway inflammation, wherein a high ratio between the subject's CysLT production and the subject's level of eosinophilic airway inflammation identifies the subject as susceptible to treatment with the leukotriene modifier.

The present invention also provides for a method of treating an inflammatory disease in a subject who has, or is at risk of developing, an inflammatory disease. This method comprises determining the subject's level of CysLT production. The method further comprises determining the subject's level of eosinophilic airway inflammation. The method further comprises determining the ratio between the subject's CysLT production and the subject's level of eosinophilic airway inflammation, wherein a high ratio between the subject's CysLT production and the subject's level of eosinophilic airway inflammation identifies the subject as susceptible to treatment with a leukotriene modifier. This method further comprises administering a leukotriene modifier to the subject if the ratio between the subject's CysLT production and the subject's level of eosinophilic airway inflammation is high.

In another aspect of the methods of the present invention, the step of determining the subject's level of CysLT production can comprise determining the subject's CysLT level selected from the group consisting of $LTE_4$, $LTC_4$, $LTD_4$ and combinations thereof.

In yet another aspect of the methods of the present invention, the step of determining the subject's level of eosinophilic airway inflammation can comprise determining the subject's fractional exhaled nitric oxide (FENO) level.

In still another aspect of the methods of the present invention, a high ratio between the subject's CysLT production and the subject's eosinophilic airway inflammation level can be in the top 75% in a range of a relevant population of subjects.

In another aspect of the methods of the present invention, a leukotriene modifier can be selected from the group consisting of a leukotriene receptor antagonist and a leukotriene synthesis inhibitor.

In another embodiment of the methods of the present invention, a leukotriene receptor antagonist can be selected from the group consisting of montelukast, zafirlukast and pranlukast.

In another aspect of the methods of the present invention, a leukotriene modifier can be an inhibitor of the 5-lipoxygenase pathway of leukotriene metabolism. The methods of the present invention also provide for a leukotriene modifier that can inhibit the activity of 5-lipoxygenase. The methods of the present invention can also provide for a leukotriene modifier that can inhibit the activity of 5-lipoxygenase-activating protein (FLAP). The methods of the present invention can also provide for Zileuton as a leukotriene modifier.

In yet another aspect of the methods of the present invention the subject can have, or can be at risk of developing, an inflammatory disease. The methods of the present invention can also provide that the subject is being administered a short-acting beta agonist to treat the inflammatory disease. The methods of the present invention can also provide that the inflammatory disease is associated with a chronic obstructive disease of the airways or can be associated with viral induced inflammation. Further the methods of the present invention can provide that the inflammatory disease is triggered by the subject's exposure to environmental conditions selected from the group consisting of tobacco smoke, diesel exhaust particles and ozone.

In still another aspect of the methods of the present invention, the step of determining the subject's CysLT level can comprise determining the subject's CysLT level in a biological fluid selected from the group consisting of urine, blood, sputum, exhaled breath condensates and bronchoalveolar fluid.

In another aspect of the methods of the present invention, the subject's FENO level can be determined by a nitric oxide analyzer.

In yet another aspect of the methods of the present invention, the subject can be human.

Another aspect of the methods of the present invention is that the subject can also be administered an inhaled corticosteroid.

The present invention also provides for a particular method to determine the susceptibility of a subject to treatment with a leukotriene modifier. This method comprises determining the subject's leukotriene $LTE_4$ level. This method further comprises determining the subject's FENO level; and determining the ratio between the subject's $LTE_4$ level and the subject's FENO level, wherein a high ratio between the subject's $LTE_4$ level and the subject's FENO level identifies the subject as susceptible to treatment with the leukotriene modifier.

The present invention also provides for a particular method of treating an inflammatory disease in a subject who has, or is at risk of developing, an inflammatory disease. This method further comprises determining the subject's leukotriene $LTE_4$ level. The method comprises determining the subject's FENO level. The method further comprises determining the ratio between the subject's $LTE_4$ level and the subject's FENO level, wherein a high ratio between the subject's $LTE_4$ level and the subject's FENO level identifies the subject as susceptible to treatment with a leukotriene modifier. This method further comprises administering a leukotriene modifier to the subject if the ratio between the subject's $LTE_4$ level and the subject's FENO level is high.

In another aspect of the methods of the present invention a high ratio between the subject's $LTE_4$ level and the subject's FENO level can be in the top 75% in a range of a relevant population of subjects.

In yet another embodiment of the methods of the present invention, the $LTE_4$ to FENO ratio can be greater than about 0.5 (pg/mg)/ppb. Still, another aspect of the methods of the present invention, the $LTE_4$ to FENO ratio can be greater than about 2.0 (pg/mg)/ppb.

Another embodiment of the methods of the present invention, the step of determining the subject's $LTE_4$ level can comprise determining the subject's $LTE_4$ level in a biological fluid selected from the group consisting of urine, blood, sputum, exhaled breath condensates and bronchoalveolar fluid.

BRIEF DESCRIPTION OF THE DRAWING

FIG. 1 shows the pathway of the major steps involved in CysLT formation derived from arachidonic acid (ARA) through the 5-lipoxygenase pathway. 5-HPETE indicates 5-hydroperoxyeicosatetraenoic.

FIGS. 2A to 2C show the effect modifiers of the montelukast effect on $LTE_4$-associated albuterol usage. Shown are the mean group estimates in the montelukast group for the baseline (BL) and treatment (TRT) intervals, with 95 percent confidence intervals, for effect modifiers of the association between albuterol use and urinary log leukotriene $E_4$ ($LTE_4$). The relationship is based on albuterol use for a given day, and the average of $LTE_4$ measurements over the prior 1 to 3 days. The estimates are plotted per interquartile (IQR) change in $LTE_4$. Illustrated are results of analyses for: (FIG. 2A) gender, (FIG. 2B) mean cotinine, first (Q1) and third (Q3) quartiles, (FIG. 2C) mean $LTE_4$ to mean FENO ratio, first (Q1) and third (Q3) quartiles.

DETAILED DESCRIPTION OF THE INVENTION

The present invention relates to a method of determining the susceptibility of a subject to treatment with a leukotriene modifier by determining the subject's cysteinyl leukotriene (CysLT) level and the subject's level of eosinophilic airway inflammation and identifying a subject with a high ratio of CysLT levels to eosinophilic airway inflammation as being susceptible to treatment with a leukotriene modifier.

An embodiment of the invention includes determination of the subject's CysLT production level. A subject's CysLT production level can be determined in a number of different ways. For example, $LTE_4$ is the stable end product of CysLT metabolism and thus serves as a marker of CysLT production. $LTE_4$ levels in a subject may be determined by any means known in the art. Typically, $LTE_4$ levels are measured in the urine after excretion by methods such as mass spectrometry, radioimmunoassays, and enzyme immunoassays, or in exhaled breath condensates. A detailed discussion of $LTE_4$ and its measurement may be found in Rabinovitch, *Immunol. Allergy Clin. N. Am.* 27:651-664 (2007), the contents of which are incorporated herein by reference in its entirety. In addition, other indicators for determining CysLT production levels include, but are not limited to, direct measurement of $LTC_4$, $LTD_4$ or $LTE_4$ levels in bronchoalveolar fluid as well as other biological fluids including but not limited to sputum (including induced sputum) and blood.

This embodiment of the present invention also includes determination of the subject's eosinophilic airway inflammation level. A subject's eosinophilic airway inflammation level can be determined in a number of ways. For example, fractional exhaled nitric oxide (FENO) is a noninvasive marker of eosinophilic airway inflammation. FENO levels in a subject may be measured or determined by any means known in the art. Typically, FENO levels are measured or determined in exhaled breath using nitric oxide analyzers, including but not limited to, chemiluminescence analyzers and electrochemical monitors, such as NIOX® (Aerocrine, Stockholm, Sweden), NIOX MINO® (Aerocrine, Stockholm, Sweden), SIEVERS® NO analyzer (Ionics Instrument, Boulder Colo.), CLD 88sp FENO analyzer (Eco Medics, Duernten, Switzerland), and LR2000 analyzer (Logan Research Ltd, Rochester, UK). A detailed discussion of FENO and its measurement may be found in Kharitonov et al., *Chest* 130:1541-1546 (2006), the contents of which are incorporated herein by reference in its entirety. In addition, other markers for determining eosinophilic airway inflammation are known in the art and include, but are not limited to, exhaled breath condensate (EBC), exhaled breath temperature, bronchial blood flow, combination biomarkers (for example: combination of the strength of the EBC approach and exhaled nitric oxide) and small molecule detection (i.e. compare detected chemical compounds in exhaled breath of subjects with and without eosinophilic airway inflammation) (Kharitonov et al., *Chest* 130:1541-1546 2006). Additionally, sputum or serum eosinophil levels can be measured to determine the eosinophilic airway inflammation level.

This embodiment of the present invention also includes determining the ratio of CysLT production to eosinophilic airway inflammation level, for example by determining the ratio of the subject's $LTE_4$ level relative to FENO level. A ratio above a threshold susceptibility level of CysLT level relative to eosinophilic airway inflammation level is considered to be high and identifies a subject as being susceptible to treatment with a leukotriene modifier. A threshold susceptibility level can be determined in a variety of ways. A threshold susceptibility level may be assessed, for example, by determining the ratio for individuals in a relevant population and then comparing the subject's ratio to the range of ratios of the individuals within the population. As discussed herein a relevant population refers to a population having one or more characteristics (e.g. demographic characteristics) in common with a subject. Such characteristics can include without limitations gender, age, exposure to viruses, exposure to environmental conditions, including but not limited to tobacco smoke, diesel exhaust particles and ozone. In this method of assessment, a subject's ratio can be considered to be high if it is in the top about 75% of the range of all the individuals in the population, about 70% of the range, about 65% of the range, about 60% of the range, about 55% of the range, about 50% of the range, about 45% of the range, about 40% of the range, about 35% of the range, about 30% of the range, about 25% of the range, about 20% of the range, about 15% of the range, about 10% of the range, about 5% of the range, about 4% of the range, about 3% of the range, about 2% of the range, or about 1% of the range.

Another method of assessment includes identifying a threshold susceptibility level by setting a standard value based on measurable parameters indicative of CysLT and eosinophilic airway inflammation levels. Values above such a standard value are considered to be high and identify a subject as being susceptible to treatment with a leukotriene modifier. For example, standard (or reference) values for a ratio of $LTE_4$ to FENO levels can be determined as discussed below. In the instance where a threshold susceptibility level is a standard value based on a $LTE_4$ to FENO ratio, a threshold susceptibility level can be a $LTE_4$/FENO ratio greater than about 0.5 (pg/mg)/ppb, greater than about 0.6 (pg/mg)/ppb, greater than about 0.7 (pg/mg)/ppb, greater than about 0.8 (pg/mg)/ppb, greater than about 0.9 (pg/mg)/ppb, greater than about 1.0 (pg/mg)/ppb, greater than about 1.1 (pg/mg)/ppb, greater than about 1.2 (pg/mg)/ppb, greater than about 1.3 (pg/mg)/ppb, greater than about 1.4 (pg/mg)/ppb, greater than about 1.5 (pg/mg)/ppb, greater than about 1.6 (pg/mg)/ppb, greater than about 1.7 (pg/mg)/ppb, greater than about 1.8 (pg/mg)/ppb, greater than about 1.9 (pg/mg)/ppb, greater than about 2.0 (pg/mg)/ppb, greater than about 2.1 (pg/mg)/ppb, greater than about 2.2 (pg/mg)/ppb, greater than about 2.3 (pg/mg)/ppb, greater than about 2.4 (pg/mg)/ppb, greater than about 2.5 (pg/mg)/ppb, greater than about 2.6 (pg/mg)/ppb, greater than about 2.7 (pg/mg)/ppb, greater than about 2.8 (pg/mg)/ppb, greater than about 2.9 (pg/mg)/ppb, greater than about 3.0 (pg/mg)/ppb, greater than about 4.0 (pg/mg)/ppb, greater than about 5.0 (pg/mg)/ppb, greater than about 6.0 (pg/mg)/ppb, greater than about 7.0 (pg/mg)/ppb, greater than about 8.0 (pg/mg)/ppb, greater than about 9.0 (pg/mg)/ppb or greater than about 10.0 (pg/mg)/ppb. It is apparent to one of skill in the art, however, that the measured values of $LTE_4$ or FENO levels may vary with the method of measurement used.

Preferably, $LTE_4$ levels can be determined by ELISA, and are greater than 1 pg/mg, greater than 2 pg/mg, greater than 3 pg/mg, greater than 4 pg/mg, greater than 5 pg/mg, greater than 6 pg/mg, greater than 7 pg/mg, greater than 8 pg/mg, greater than 9 pg/mg, greater than 10 pg/mg, greater than 20 pg/mg, greater than 30 pg/mg, greater than 40 pg/mg, greater than 50 pg/mg, greater than 60 pg/mg, greater than 70 pg/mg, greater than 80 pg/mg, greater than 90 pg/mg, greater than 100 pg/mg, greater than 200 pg/mg, greater than 300 pg/mg, greater than 400 pg/mg, greater than 500 pg/mg, greater than 1000 pg/mg, or greater than 1500 pg/mg (standardized per milligram of creatinine).

Preferably, FENO levels can be determined by exhaled breath using a nitric oxide analyzer, and are less than about 500 ppb, less than about 475 ppb, less than about 450 ppb, less than about 425 ppb, less than about 400 ppb, less than about 375 ppb, less than about 350 ppb, less than about 325 ppb, less than about 300 ppb, less than about 275 ppb, less than about 250 ppb, less than about 225 ppb, less than about 200 ppb, less than about 175 ppb, less than about 150 ppb, less than about 125 ppb, less than about 100 ppb, less than about 95 ppb, less than about 90 ppb, less than about 85 ppb, less than about 80 ppb, less than about 75 ppb, less than about 70 ppb, less than about 65 ppb, less than about 60 ppb, less than about 55 ppb, less than about 50 ppb, less than about 45 ppb, less than about 40 ppb, less than about 35 ppb, less than about 30 ppb, less than 29 ppb, less than 28 ppb, less than 27 ppb, less than 26 ppb, less than 25 ppb, less than 24 ppb, less than 23 ppb, less than 22 ppb, less than 21 ppb, less than 20 ppb, less than 19 ppb, less than 18 ppb, less than 17 ppb, less than 16 ppb, less than 15 ppb, less than 14 ppb, less than 13 ppb, less than 12 ppb, less than 11 ppb, less than 10 ppb, less than 9 ppb, less than 8 ppb, less than 7 ppb, less than 6 ppb, less than 5 ppb, less than 4 ppb, less than 3 ppb, less than 2 ppb or less than 1 ppb.

In some embodiments, a baseline CysLT to eosinophilic airway inflammation ratio for a given individual can be determined and changes in the ratio are monitored over time. In such an instance the baseline will be the threshold susceptibility level. Increases in the CysLT/eosinophilic airway inflammation ratio from the baseline value are considered to be high and may be used to identify when a subject will have increased susceptibility to treatment with leukotriene modifiers.

A further embodiment of the present invention is a method to determine the susceptibility of a subject to treatment with a leukotriene modifier. This method comprises determining the subject's leukotriene $LTE_4$ level, and determining the subject's FENO level, and determining the ratio between the subject's $LTE_4$ level and the subject's FENO level. A high ratio between the subject's $LTE_4$ level and the subject's FENO level identifies the subject as susceptible to treatment with the leukotriene modifier.

Various definitions and aspects of the invention will be described below, but the invention is not limited to any specific embodiments that may be used for illustrative or exemplary purposes.

A leukotriene modifier includes any agent that modifies or inhibits the inflammatory activities of leukotrienes. Such modifications or inhibitions can take place at a variety of levels. For example, the inflammatory activity of a leukotriene can be modified or inhibited by modifying or inhibiting leukotriene metabolism. For example, leukotriene metabolism can be effectuated by inhibition of 5-lipoxygenase or inhibition of 5-lipoxygenase-activating protein (FLAP) (e.g., Zileuton also known as ZYFLO® Abbott Laboratories, Abbott Park, Ill.). The inflammatory activity of a leukotriene can alternatively be modified or inhibited by modifying or inhibiting biological functioning of leukotrienes and CysLTs. For example, inhibition of the biological functioning of leukotrienes can be effectuated by agents that antagonize the actions of leukotriene receptors, including CysLT receptors, (also known as leukotriene receptor antagonists or LTRAs). LTRAs include but are not limited to montelukast, zafirlukast (e.g. ACCOLATE® AstraZeneca, Wilmington Del.) and pranlukast. The biological functioning of leukotrienes can also be inhibited by interference with receptor binding such as by an antibody to a leukotriene or antibody to a CysLT.

In the methods of the present invention, the subject may have, or be at risk of developing, an inflammatory disease, and, in particular, diseases associated with airway inflammation. For example, airway inflammation is commonly associated with allergic inflammation and/or viral-induced inflammation. The subject may thus have, or be at risk of developing, a condition including, but not limited to, any chronic obstructive disease of the airways. Such conditions include, but are not limited to any one or more of the following: asthma, chronic obstructive pulmonary disease, allergic bronchopulmonary aspergillosis, hypersensitivity pneumonia, eosinophilic pneumonia, emphysema, bronchitis, allergic bronchitis bronchiectasis, cystic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma and parasitic lung disease. Airway inflammation associated with viral-induced inflammation can occur in a patient that has, or is at risk of developing, an infection by a virus including, but not limited to any one or more of the following: respiratory syncytial virus (RSV), parainfluenza virus (PIV), rhinovirus (RV) and adenovirus. Additionally, exposure to environmental conditions, including but not limited to any one or more of the following: tobacco smoke, diesel exhaust particles and ozone may trigger asthma in the subject.

The methods of the present invention can be used in any animal subject, and particularly, in any vertebrate mammal, including, but not limited to, primates, rodents, livestock and domestic pets. Preferred mammals for the methods of the present invention include humans and even more preferably, female humans.

Another embodiment of the present invention is a method of treating an inflammatory disease in a subject who has, or is at risk of developing, an inflammatory disease. This method comprises determining the subject's level of CysLT production, and determining the subject's level of eosinophilic airway inflammation. The method further comprises determining the ratio between the subject's CysLT production and the subject's level of eosinophilic airway inflammation, wherein a high ratio between the subject's CysLT production and the subject's level of eosinophilic airway inflammation identifies the subject as susceptible to treatment with a leukotriene modifier. This method further comprises administering a leukotriene modifier to the subject if the ratio between the subject's CysLT production and the subject's level of eosinophilic airway inflammation is high. Suitable leukotrienes for administration are discussed above and methods of administration of them are known. In a more specific embodiment, the present invention includes a method of teating an inflammatory disease in a subject who has, or is at risk of developing, an inflammatory disease. This method comprises determining the subject's leukotriene $LTE_4$ level, and determining the subject's FENO level. The method further comprises determining the ratio between the subject's $LTE_4$ level and the subject's FENO level, wherein a high ratio between the subject's $LTE_4$ level and the subject's FENO level identifies the subject as susceptible to treatment with a leukotriene modifier. This method further comprises administering a leukotriene modifier to the subject if the ratio between the subject's $LTE_4$ level and the subject's FENO level is high.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Example 1

This example evaluates the differences in CysLT levels between individuals and asthma control. In the experiments described below, a randomized-placebo-controlled study showed that increased albuterol usage among school children is associated with changes in CysLT levels (as defined by urinary $LTE_4$ excretion) and attenuated after randomization to treatment with montelukast.

Children received 22% more albuterol per IQR (interquartile range) increase in $LTE_4$. Since the approximate mean albuterol use in these children was 2 puffs per day, on average, children received 13 extra puffs per month when $LTE_4$ levels were high compared to when they were low. In the example below, the children were followed in a relatively well-controlled setting over consecutive days. As such, there was limited variability in $LTE_4$ and albuterol usage. Assuming a linear relationship, this percent change relationship could be extrapolated to different settings in order to estimate, for example, the magnitude of $LTE_4$ increase in predicting an asthma exacerbation.

By utilizing a repeated measures model, this experiment is able to illustrate how between-subject variability in CysLT effects can be related to the heterogeneous response observed with montelukast treatment. As such, increases in urinary $LTE_4$ during the baseline interval were related to increased albuterol usage only among certain subgroups of children. Consequently, after montelukast treatment was initiated, there were significant changes in $LTE_4$-related albuterol usage in some and little change in other children. In this context, girls demonstrated significantly increased $LTE_4$-related albuterol usage during the baseline interval. During the subsequent treatment interval, this association was significantly attenuated in girls only and near-significant modification of this attenuation effect was observed between female and male groups.

The panel design in this experiment with multiple repeated measurements is well suited to detect susceptible subgroups or individuals since within-subject exposure—response relationships can be determined with great precision (Delfino, R J. Who are the children with asthma most susceptible to air pollution? *Am J Respir Crit Care Med* 2006; 173: 1054-1055). This allowed for significant observations despite the small number of subjects.

Subjects:

Twenty-eight children, aged 6 to 15, who had physician-diagnosed asthma were followed over a 5-month period (Nov. 15, 2005 to Apr. 15, 2006). Children were excluded from the study if they were already receiving montelukast. Many of the children are classified as urban poor. The children attended the same school.

Protocol:

After an initial two and a half month period (baseline interval), children were randomized to receive daily montelukast (montelukast group) or placebo (placebo group) for the final two and a half months of the study (treatment interval). Study medication and placebo were administered in a single-blinded fashion by school nurses or study personnel on school days and by parents (who were blinded) on non-school-days. Children were otherwise followed by their regular physicians who were free to adjust medications as needed (these medication changes were recorded and controlled for in the statistical analysis).

Medication Monitoring:

Each child was given a Doser (Meditrak, Hudson, M S) for use at school throughout the 5-month period. The Doser is an electronic counter that records the total number of (albuterol) activations in each 24-hour period. At study initiation, parents completed a questionnaire describing baseline demographic and asthma severity characteristics. School nurses recorded all other medication changes during the study.

Urine Collection:

Sixteen urine samples were collected from each child on 8 consecutive schooldays during the baseline interval and 8 consecutive schooldays during the treatment interval. Urine was collected at approximately the same time each day (10:00 AM to 12:00 PM). Collection was staggered in groups of 10 children so that urine monitoring occurred daily throughout the 5 months of the study.

$LTE_4$ and Cotinine Measurements:

Urinairy $LTE_4$ and cotinine were measured as previously described (Westcott J Y, Maxey K M, Macdonald J, Wenzel S E. Immunoaffinity resin for purification of urinary leukotriene E4. *Prostaglandins Other Lipid Mediat* 1998; 55: 301-21; North L M, Gaudette N D, Cordeiro M L, Fitchen J H, Davidson S L, Hindahl M S. Detection of cotinine in oral fluid recovered with the OraSure collection system. *Ann NY Acad Sci* 1993 Sep. 20; 694: 332-3). Urine $LTE_4$ levels were reported in picograms (pg) and standardized per milligram (mg) of creatinine. Urine cotinine levels were reported in nanograms (ng) per milliliter and standardized per mg of creatinine.

Fractional Exhaled Nitric Oxide (FENO) Measurement:

Each child performed up to 16 FENO measurements on a NIOX® device (Aerocrine, Stockholm, Sweden) at approximately the same time as urine collection. Standard flow-rates (50 l/sec) and length of collection (6-seconds) were utilized (Buchvald F, Baraldi E, Carraro S, Gaston B, De Jongste J, Pijnenburg M W, Silkoff P E, Bisgaard H. Measurements of exhaled nitric oxide in healthy subjects age 4 to 17 years. *J Allergy Clin Immunol* 2005 June; 115(6): 1130-6).

Statistical Analysis:

Baseline model: A Poisson regression model employing generalized estimating equations (GEE) (Dobson A J. An introduction to generalized linear models, $2^{nd}$ edition, Chapman & Hall/CRC 2001) was used to determine the strength of association between albuterol medication use (modeled as the outcome) and $LTE_4$ levels, at various lag times (in days) between the variables. An indicator for Friday (=1 if response was on Friday, =0 otherwise) was included because children had regular exercise activities from Monday through Thursday, but not on Friday. Consequently, subjects used significantly less albuterol on Fridays. The same day and up to a 4-day lag of $LTE_4$ was tested for, in separate models.

Experiment model: Daily albuterol use was modeled as a function of $LTE_4$, group (montelukast and placebo), interval (baseline and treatment), and all interactions of these variables, using Poisson regression and employing GEE. Using the baseline model as a guide, 3-day moving averages of $LTE_4$ (days 0-2 and 1-3 prior to current day) were used. Other covariates in the model included daily indicators for Friday, prednisone use, special exercise days during the treatment interval, and interval-level indictors of ICS and LABA use.

Effect modifier models: These models were fit for the subjects randomized to montelukast only. The model had $LTE_4$, interval, the effect modifier of interest, and all interactions of these variables. Otherwise, the model was similar to the 'Experiment model' described above. The effect modifiers tested included gender, ICS and LABA use, mean $LTE_4$, mean FENO, height, mean cotinine, and mean $LTE_4$ to FENO ratio.

The interquartile range (IQR) for $LTE_4$ was used to standardize slope estimates; this statistic was determined by first calculating the IQR for each subject, and then taking the median across subjects. For all models described above, a first order autoregressive working covariance structure was used to model repeated measures within subjects over time. SAS software, version 9.1 (PROC GENMOD) was used to fit the data to the models described above. Because of the tendency for standard errors (SE) of beta estimates in GEE models to be underestimated for small sample sizes, SEs for all models were adjusted using Kauermann and Carroll's correction factor (Kauermann G, Carroll, R J. A note on the efficiency of sandwich covariance matrix estimation. *JASA* 2001; 96: 1387-1398; Lu B, Preisser J S, Qaqish B F, Suchindran C, Bangdiwala S I, Wolfson M. A comparison of two bias-corrected covariance estimators for generalized estimating equations. *Biometrics* 2007 September; 63(3): 935-41).

Results: Demographics:

All children completed the 5-month protocol. One child, randomized to placebo, was started on montelukast by their physician and therefore was not included in the analysis. Table 1 below summarizes the demographic and asthma severity information in the remaining children based on a pre-study questionnaire. Montelukast and placebo groups were comparable with respect to these variables including gender (p=0.21) and symptom severity (p=0.53).

TABLE 1

| | | | | | | ICS | |
|---|---|---|---|---|---|---|---|
| | | | | | As-needed | Usage (includes | ICS and |
| | | | | Symptom | albuterol | ICS and | LABA |
| | | Age | Male n | nights/week | days/week | LABA) n | only n |
| Group | n | (range) | (%) | n (%)* | n (%)* | (%) | (%) |
| Montelukast | 14 | 11 (7-15) | 8 (57) | <2: 7 (50) | 0: 4 (28) | 12 (86) | 7 (50) |
| | | | | 2-3: 4 (29) | 1-2: 8 (57) | | |
| | | | | >3: 3 (21) | >2: 2 (14) | | |
| Placebo | 13 | 11 (7-13) | 11 (85) | <2: 4 (31) | 0: 3 (23) | 10 (77) | 3 (23) |
| | | | | 2-3: 7 (54) | 1-2: 8 (61) | | |
| | | | | >3: 2 (15) | >2: 2 (15) | | |

*previous year's average

Results: Biomarker Levels $LTE_4$ measurements were carried out on 387 collected urine samples (186 and 201 in the baseline and treatment intervals, respectively) and 386 FENO measurements (Table 2). Across groups and intervals, the median subject IQR for $LTE_4$ was 31 pg/mg creatinine, which was used as the standard increase for albuterol change estimates.

TABLE 2

Median and IQR statistics for $LTE_4$, FENO, Cotinine and $LTE_4$/FENO ratios by treatment group and interval.

| Variable | Placebo, Baseline | Montelukast, Baseline | p-value* | Placebo, Treatment | Montelukast, Treatment | p-value* |
|---|---|---|---|---|---|---|
| LTE4† | 69.6 (34.0) | 75.4 (33.5) | 0.98 | 87.1 (24.0) | 78.9 (29.5) | 0.73 |
| FENO† | 20.7 (3.85) | 31.6 (12.9) | 0.07 | 19.4 (4.14) | 34.9 (13.3) | 0.14 |
| Cotinine† | 1.39 (0.7) | 3.57 (1.55) | 0.11 | 1.63 (1.00) | 3.08 (2.2) | 0.37 |
| LTE4/FENO†† | 4.87 (2.06) | 2.63 (2.17) | 0.05 | | | |

†Median subject average (median subject IQR). Statistics were determined by calculating averages and IQRs within subjects first, and then taking the median across subjects.
††Median $LTE_4$/FENO ratio (IQR $LTE_4$/FENO ratio). The ratio variable was calculated for each subject as the mean $LTE_4$, divided by the mean FENO, using all values during the interval. Median and IQR statistics were then calculated across subjects.
*Between-group difference for the interval, using a Wilcoxon Rank-Sum test.

Results: Relationship Between Albuterol Use and $LTE_4$ Increases

During the baseline interval, mean (standard deviation) albuterol puffs per day were 1.8 (1.1) for the placebo group and 2.2 (0.8) for the montelukast group. Urine $LTE_4$ levels measured in all subjects during the baseline interval were strongly associated with increased albuterol use (21.9% increase in albuterol usage per $LTE_4$ IQR increase, p=0.003) 2 days after urine collection (Day 2) (Table 3). Of interest, the strength of this CysLT-albuterol interaction at baseline and subsequent response to montelukast was not uniform over all groups. Responses tended to be greater in girls than boys and children exposed to higher levels of environmental tobacco smoke (ETS) demonstrated greater susceptibility to montelukast than those with lower ETS exposures.

TABLE 3

Albuterol Usage Change per LTE4 IQR Increase During the Baseline Interval (All Subjects)

| Day | Number of Subject-Day Observations | Change in Albuterol Usage per LTE4 IQR (95th CI) | p-Value |
|---|---|---|---|
| 0 | 186 | 7.5% (0.4, 15.1) | 0.04 |
| 1 | 148 | 9.2% (−1.7, 21.2) | 0.10 |
| 2 | 108 | 21.9% (7.0, 39.0) | 0.003 |
| 3 | 82 | 3.5% (−5.9, 13.8) | 0.48 |
| 4 | 68 | 5.8% (−3.3, 15.8) | 0.22 |

Example 2

This example illustrates that less albuterol use is needed after montelukast treatment in subjects having high CysLT/eosinophilic airway inflammation ratio compared to subjects with lower ratios.

The efficacy of montelukast treatment on $LTE_4$-related albuterol usage (i.e. increase in albuterol usage per IQR change in $LTE_4$) was examined. Based on results from the previous analysis, the primary lag structure used in these models was a 3-day moving average, from Days 1 to 3, which was centered on the day with the largest observed effect (Day 2). Also analyzed was the 3-day moving average from Days 0 through 2. The moving average often reduces variability in estimates compared with considering individual days.

For the Day 1-3 moving average, albuterol usage increased 11.3% per IQR increase in $LTE_4$ (p=0.04) during the baseline interval for the montelukast group (Table 4). During the treatment interval, this relationship was not apparent (−3.2%, p=0.44), and the relative change in associations between intervals for this group was significant (p=0.0005). For children in the placebo group, albuterol usage per IQR increase in $LTE_4$ was 4.6% and 7.0% in the baseline and treatment intervals, respectively (p=0.80 for relative difference).

Using the Day 0-2 moving average, albuterol usage increased 20.5% (p<0.01) and 8.8% (p=0.24) per IQR increase in $LTE_4$ for the placebo and montelukast groups, respectively, during the baseline period. Similar statistics were not significant during the treatment interval for either group (5.9%, p=0.56 for placebo; −3.0%, p=0.50 for montelukast). Despite the large baseline value for the placebo group, the relative difference in statistics between intervals was not significant for the placebo group (p=0.19), while the relative difference was significant for the montelukast group (p=0.05).

TABLE 4

Change in Albuterol Usage Per IQR Increase in LTE4 ((5% CI) (entries expressed as %)

| | | Lag 1-3 | | | | Lag 0-2 | | | |
|---|---|---|---|---|---|---|---|---|---|
| Group | | Baseline Interval | Treatment Interval | Relative difference† | p†† | Baseline Interval | Treatment Interval | Relative difference† | p†† |
| MK | | 11.3 (0.4, 23.4) | −3.2 (−10.8, 5.1) | −13.0 (−19.6, −5.9) | 0.0005 | 8.8 (−5.4, 25.1) | −3.0 (−11.2, 5.9) | −10.8 (−20.3, −0.1) | 0.05 |

TABLE 4-continued

Change in Albuterol Usage Per IQR Increase in LTE4 ((5% CI)
(entries expressed as %)

| Group | Lag 1-3 | | | | Lag 0-2 | | | |
|---|---|---|---|---|---|---|---|---|
| | Baseline Interval | Treatment Interval | Relative difference† | p†† | Baseline Interval | Treatment Interval | Relative difference† | p†† |
| PL | 4.6 (−4.8, 15.0) | 7.0 (−4.9, 20.3) | 2.2 (−13.4, 20.7) | 0.80 | 20.5 (3.0, 41.1) | 5.9 (−12.8, 28.6) | −12.1 (−27.6, 6.7) | 0.19 |

†Determined as the fold change in albuterol usage per IQR increase in the treatment interval, divided by the fold change in albuterol usage per IQR increase in the baseline interval, and expressed here as percentage change by subtracting 1.
††p-value for relative difference estimate.
MK = Montelukast and
PL = Placebo Predictors of Susceptibility:

Utilizing the 1-3 day moving average effect model which had provided the most robust estimates in the experiment model, predictors of susceptibility to CysLT-related albuterol usage and to montelukast treatment were then assessed as listed in Table 5 (use of combination controller medication (i.e. ICS with LABA), height or age, gender, tobacco exposure as measured by mean urine cotinine levels, mean LTE4 level, mean FENO level and mean LTE4 to FENO ratio level). Values utilized were from the baseline interval only to ensure that these levels were unaffected by montelukast treatment. Estimates of all these variables are summarized in Table 5.

increase in albuterol usage per $LTE_4$ IQR (p=0.004) while boys' relative albuterol usage increased by 8.0% (p=0.32). Reflecting these differences in CysLT-related albuterol usage, declines in $LTE_4$-related albuterol usage with montelukast treatment tended to be greater in girls than boys (p=0.01 for girls, p=0.21 for boys, p=0.07 for between-group interaction comparing declines) (FIG. 2A). Children in the $3^{rd}$ quartile for urine cotinine demonstrated an 11.8% increase in albuterol usage per $LTE_4$ IQR at baseline (p=0.07) while $LTE_4$-related albuterol usage was increased by 4.6% among children in the $1^{st}$ cotinine quartile (p=0.41). Declines in

TABLE 5

Predictors of Susceptibility to Montelukast

| Predictor | Interval or Comparison | Group 1 or 1st Quartile Estimate of Change in Albuterol Usage per IQR of LTE4, expressed as % | Group 2 or 3rd Quartile Estimate of Change in Albuterol Usage per IQR of LTE4, expressed as % | Effect modifier p-value†† |
|---|---|---|---|---|
| No Meds or ICS (Group 1 meds) Vs ICS and LABA (Group 2 meds) | Baseline Treatment Relative Diff. † | 14.8 (p = 0.11) −10.5 (p = 0.35) −22.0 (p = 0.10) | 6.0 (p = 0.56) −1.0 (p = 0.75) −6.6 (p = 0.36) | 0.27 |
| Height | Baseline Treatment Relative Diff. † | 16.7 (p = 0.12) −2.4 (p = 0.57) −16.4 (p = 0.04 **) | 19.3 (p = 0.09 *) −0.3 (p = 0.96) −16.4 (p = 0.04 **) | 0.99 |
| LTE4 | Baseline Treatment Relative Diff. † | 13.7 (p = 0.35) −1.5 (p = 0.92) −13.4 (p = 0.36) | 6.8 (p = 0.45) −4.8 (p = 0.47) −10.9 (p = 0.25) | 0.83 |
| FENO | Baseline Treatment Relative Diff. † | 11.5 (p = 0.07 *) −0.1 (p = 0.99) −10.4 (p = 0.17) | −5.9 (p = 0.74) −6.4 (p = 0.22) −0.6 (p = 0.98) | 0.68 |
| LTE4:FENO Ratio | Baseline Treatment Relative Diff. † | −2.6 (p = 0.79) −0.8 (p = 0.87) 1.8 (p = 0.89) | 19.7 (p = 0.03 **) −1.3 (p = 0.80) −17.6 (p = 0.05 *) | 0.25 |
| Male (Group 1 gender) Vs Female (Group 2 gender) | Baseline Treatment Relative Diff. † | 8.0 (p = 0.32) −0.5 (p = 0.92) −7.9 (p = 0.21) | 20.7 (p = 0.004 **) −11.5 (p = 0.25) −26.7 (p = 0.01 **) | 0.07 * |
| Cotinine | Baseline Treatment Relative Diff. † | 4.6 (p = 0.41) −4.0 (p = 0.25) −8.2 (p = 0.18) | 11.8 (p = 0.07 *) −3.6 (p = 0.29) −6.6 (p = 0.01 **) | 0.04 ** |

† Determined as the fold change in albuterol usage per IQR increase in the treatment interval, divided by the fold change in albuterol usage per IQR increase in the baseline interval, and expressed here as percentage change by subtracting 1.
††LTE4 -by- interval -by- predictor interaction
* p < 0.1
** p < 0.05

Demographic Markers:

Among the variables tested, gender was a near significant modifier while cotinine levels were significant modifiers of the montelukast and $LTE_4$-related albuterol relationship. During the baseline interval, girls demonstrated a 20.7%

$LTE_4$-related albuterol usage after montelukast treatment were significant (p=0.01) among children with higher cotinine but not the lower cotinine quartile (p=0.18 for low cotinine group) and the interaction between groups was significant (p=0.04 for interaction between groups) (FIG. 2B).

Biomarkers:

During the baseline interval, $LTE_4$ levels were significantly but weakly correlated with same day FENO levels (r=0.38 for placebo group, p=0.0003. r=0.27, p=0.015 for the montelukast group). Mean $LTE_4$ levels did not predict susceptibility nor were any trends observed at baseline or after treatment. $LTE_4$-related albuterol usage at baseline was near significant for children in the $1^{st}$ FENO quartile (11.5% increase per $LTE_4$ IQR, p=0.07 for $1^{st}$ quartile, 5.9% decrease, p=0.74 for $3^{1d}$ quartile) but relative differences between intervals were not significant in either group (p=0.17 for $1^{st}$ quartile, p=0.98 for $3^{rd}$ quartile (p=0.68 for between-group interaction).

Children in the $3^{rd}$ quartile for $LTE_4$ to FENO ratio demonstrated a 19.7% increase in albuterol usage per $LTE_4$ IQR at baseline (p=0.03) while $LTE_4$-related albuterol usage decreased by 2.6% per $LTE_4$ IQR among children in the $1^{st}$ ratio quartile (p=0.79) during this interval. Declines in $LTE_4$-related albuterol usage after montelukast treatment were significant among children in the $3^{rd}$ $LTE_4$ to FENO quartile (p=0.0) but not the $1^{st}$ quartile (p=0.89). However, between-group interactions for these declines were not significantly different (p=0.25) (FIG. 2C). Children with low FENO relative to urine $LTE_4$ levels demonstrated significant associations between $LTE_4$ and albuterol usage during baseline interval and significant attenuation of these associations during montelukast treatment.

The foregoing description of the present invention has been presented for purposes of illustration. The description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Each publication and reference cited herein is incorporated herein by reference in its entirety.

What is claimed is:

1. A method of treating an inflammatory disease in a human subject who has, or who is at risk of developing, an inflammatory disease, comprising:
   a. obtaining a fluid sample from the subject;
   b. measuring the $LTE_4$ level in the fluid sample by a method selected from the group consisting of mass spectrometry, radioimmunoassay and enzyme immunoassay;
   c. measuring the subject's FENO level; and
   d. administering a leukotriene modifier to a subject having a ratio of LTE4 to FENO of greater than about 0.5 (pg/mg)/ppb.

2. The method of claim 1, wherein the subject is being administered a short-acting beta agonist to treat the inflammatory disease.

3. The method of claim 1, wherein the inflammatory disease is associated with a chronic obstructive disease of the airways.

4. The method of claim 1, wherein the inflammatory disease is triggered by the subject's exposure to environmental conditions selected from the group consisting of tobacco smoke, diesel exhaust particles and ozone.

5. The method of claim 1, wherein the inflammatory disease is associated with viral induced inflammation.

6. The method of claim 1, wherein the subject's FENO level is determined by a nitric oxide analyzer.

7. The method of claim 1, wherein the fluid sample is urine.

8. The method of claim 1, wherein the subject is being administered an inhaled corticosteroid.

9. The method of claim 1, wherein the ratio is greater than about 2.0 (pg/mg)/ppb.

10. The method of treating an inflammatory disease comprising administering a leukotriene modifier to a human subject that has been determined to have a LTE4 to FENO ratio greater than about 0.5 (pg/mg)/ppb.

11. The method of claim 10, wherein the inflammatory disease is associated with a chronic obstructive disease of the airways.

12. The method of claim 11, wherein the inflammatory disease is triggered by the subject's exposure to environmental conditions selected from the group consisting of tobacco smoke, diesel exhaust particles and ozone.

13. The method of claim 11, wherein the inflammatory disease is associated with viral induced inflammation.

14. The method of claim 11, wherein the leukotriene modifier is selected from the group consisting of a leukotriene receptor antagonist and a leukotriene synthesis inhibitor.

15. The method of claim 11, wherein the leukotriene modifier is an inhibitor of the 5-lipoxygenase pathway of leukotriene metabolism.

* * * * *

UNITED STATES PATENT AND TRADEMARK OFFICE
CERTIFICATE OF CORRECTION

PATENT NO. : 9,383,374 B2
APPLICATION NO. : 14/177441
DATED : July 5, 2016
INVENTOR(S) : Nathan Rabinovitch and Erwin Gelfand Page 1 of 1

It is certified that error appears in the above-identified patent and that said Letters Patent is hereby corrected as shown below:

In the claims:

In Claim 12, Column 18, Line 34, please delete "claim 11" and insert --claim 10--

In Claim 13, Column 18, Line 38, please delete "claim 11" and insert --claim 10--

In Claim 14, Column 18, Line 40, please delete "claim 11" and insert --claim 10--

In Claim 15, Column 18, Line 43, please delete "claim 11" and insert --claim 10--

Signed and Sealed this
Twenty-third Day of August, 2016

Michelle K. Lee
*Director of the United States Patent and Trademark Office*